United States Patent [19]
Delroisse et al.

[11] Patent Number: 6,140,294
[45] Date of Patent: Oct. 31, 2000

[54] BLEACH AND OXIDATION CATALYST

[75] Inventors: Michel Gilbert Delroisse, Wirral, United Kingdom; Bernard Lucas Feringa, Groningen, Netherlands; Ronald Hage, Vlaardingen, Netherlands; Roelant Mathijs Hermant, Vlaardingen, Netherlands; Robertus Everardus Kalmeijer, Vlaardingen, Netherlands; Jean Hypolites Koek, Vlaardingen, Netherlands; Christiaan Lamers, Vlaardingen, Netherlands; Minze Theunis Rispens, Groningen, Netherlands; Stephen William Russell; Ronaldus Theodorus Vliet, both of Vlaardingen, Netherlands; Jane Whittaker, Wirral, United Kingdom

[73] Assignee: Unilever Home & Personal Care USA, division of Conopco, Inc., Greenwich, Conn.

[21] Appl. No.: 09/433,157

[22] Filed: Nov. 3, 1999

[30] Foreign Application Priority Data

Nov. 10, 1998 [EP] European Pat. Off. .............. 98309169

[51] Int. Cl.[7] ................................. C11D 7/18; C11D 7/54
[52] U.S. Cl. .......................... 510/309; 510/302; 510/303; 510/310; 510/311; 510/312; 510/372; 510/376; 510/378; 510/508; 252/186.28; 252/186.29; 252/186.33; 502/165; 502/167

[58] Field of Search ..................................... 510/302, 303, 510/309, 310, 311, 312, 372, 376, 378, 508; 252/186.28, 186.29, 186.33; 502/165, 167

[56] References Cited

U.S. PATENT DOCUMENTS

| 5,580,485 | 12/1996 | Feringa et al. ............................ 510/311 |
| 5,630,906 | 5/1997 | Boe et al. ................................. 162/74 |

FOREIGN PATENT DOCUMENTS

| 0 458 398 | 11/1991 | European Pat. Off. . |
| 0 909 809 | 10/1997 | European Pat. Off. . |
| 2 692 499 | 12/1993 | France . |
| 196 05 688 | 2/1996 | Germany . |
| 197 13 851 | 4/1997 | Germany . |
| 95/34628 | 12/1995 | WIPO . |
| 97/18035 | 5/1997 | WIPO . |
| 97/48787 | 12/1997 | WIPO . |

Primary Examiner—Gregory R. Delcotto
Attorney, Agent, or Firm—Milton L. Honig

[57] ABSTRACT

A bleach and oxidation catalyst is provided comprising a catalytically active iron, manganese or copper complex including a specified pentadentate nitrogen-containing ligand. The metal complex can activate hydrogen peroxide or peroxyacids and provides favourable stain removal properties. In addition, a considerably improved stability of these metal complex compounds in alkaline aqueous environment has been obtained, in particular at the peroxy compound concentrations generally present in the fabric washing liquor.

17 Claims, No Drawings

BLEACH AND OXIDATION CATALYST

FIELD OF THE INVENTION

This invention relates to bleach and oxidation catalysts, to compositions containing such catalysts, especially bleaching and detergent bleaching compositions, and to methods of bleaching and cleaning substrates, especially fabric substrates, using such catalysts. In particular, the present invention is concerned with catalytic complexes comprising a pentadentate ligand coordinated to an iron, manganese or copper ion, for use with peroxygen bleaching agents.

BACKGROUND OF THE INVENTION

Peroxygen bleaching agents have been known for many years and are used in a variety of industrial and domestic bleaching and cleaning processes. The activity of such agents is, however, extremely temperature-dependent, and drops off sharply at temperatures below 60° C. Especially for cleaning fabrics, high temperature operation is both economically undesirable and practically disadvantageous.

One approach to solving this problem has been through the additional use of so-called bleach activators, also known as bleach precursors. These activators typically are carboxylic acid esters that react with hydrogen peroxide anions in aqueous liquor to generate the corresponding peroxyacid which, in turn, oxidises the substrate. However, these activators are not catalytic. Once the activator has been perhydrolysed, it can no longer be recycled and, therefore, it is usually necessary to use relatively high levels of activator. Since bleach activators are relatively expensive, the cost of using activators at such levels may be prohibitive.

Another approach has been to use transition metal complexes as catalysts to activate the peroxy bleaching agent. For example, U.S. Pat. No. 4,728,455 discloses the use of manganese(III)-gluconate as a peroxide bleach catalyst with high hydrolytic and oxidative stability. In EP-A-0,458,379, for example, triazacyclononane-based manganese complexes are disclosed that display a high catalytic oxidation activity at low temperatures, which is particularly suitable for bleaching purposes.

In WO-A-9534628, it has been shown that the use of iron complexes containing certain pentadentate nitrogen-containing ligands, in particular N,N-bis(pyridin-2-ylmethyl)bis(pyridin-2-yl)methylamine ("$N_4Py$"), as bleaching and oxidation catalysts, resulted in favourable bleaching and oxidation activity. However, the synthesis of this ligand is relatively costly.

WO-A-9718035 discloses iron and manganese complexes containing ligands such as N,N'-bis(pyridin-2-ylmethyl) ethylene-1,2-diamine ("Bispicen"), N-methyl-N,N',N'-tris(pyridin-2-ylmethyl)ethylene-1,2-diamine ("TrispicMeen"), and N,N,N',N'-tetrakis(pyridin-2-ylmethyl)ethylene-1,2-diamine ("TPEN"), as peroxide oxidation catalysts for organic substrates.

WO-A-9748787 relates to iron complexes having polydentate ligands containing at least six nitrogen or oxygen hetero atoms, the metal ion being coordinated by at least five hetero atoms, for example 1,1,4,8,11,11-hexa(pyridin-2-ylmethyl)-1,4,8,11-tetra-aza-undecane ("Hptu"), as catalysts for peroxide, peroxyacid and molecular oxygen bleaching and oxidation.

Whilst known transition metal complexes have to an extent been used successfully as catalysts in bleaching or oxidation processes, there remains a need for other bleaching and oxidation catalysts, preferably that are more effective in terms of activity or cost.

We have now surprisingly found that a significant or improved catalytic activity can be achieved by an iron, manganese or copper complex having a pentadentate ligand comprising substituted heteroaryl groups. Furthermore, we have found that catalysts exhibiting such activity can be produced by easily accessible syntheses.

SUMMARY OF THE INVENTION

Accordingly, in one aspect, the present invention provides a bleach and oxidation catalyst comprising a complex of the general formula (A):

in which

M represents iron in the II, III, IV or V oxidation state, manganese in the II, III, IV, VI or VII oxidation state, or copper in the I, II or III oxidation state;

X represents a coordinating species;

n represents zero or an integer in the range from 0 to 3;

z represents the charge of the complex and is an integer which can be positive, zero or negative;

Y represents a counter ion, the type of which is dependent on the charge of the complex;

q=z/[charge Y];

L represents a pentadentate ligand of general formula (B):

wherein each $R^1$ independently represents —$R^3$—V, in which $R^3$ represents optionally substituted alkylene, alkenylene, oxyalkylene, aminoalkylene or alkylene ether, and V represents a substituted heteroaryl group selected from pyridinyl, pyrazinyl, pyrazolyl, imidazolyl, benzimidazolyl, pyrimidinyl, triazolyl and thiazolyl;

W represents an optionally substituted alkylene bridging group selected from —$CH_2CH_2$—, —$CH_2CH_2CH_2$—, —$CH_2CH_2CH_2CH_2$—, and —$CH_2$—$C_6H_4$—$CH_2$—;

$R^2$ represents a group selected from alkyl, aryl and arylalkyl, optionally substituted with a substituent selected from hydroxy, alkoxy, carboxylate, carboxamide, carboxylic ester, sulphonate, amine, alkylamine and $N^+(R^4)_3$, wherein $R^4$ is selected from hydrogen, alkanyl, alkenyl, arylalkanyl, arylalkenyl, oxyalkanyl, oxyalkenyl, aminoalkanyl, aminoalkenyl, alkanyl ether and alkenyl ether.

In another aspect, the present invention provides a bleaching composition comprising a peroxy bleaching compound and a catalyst as defined above. The peroxy bleaching compound is preferably selected from hydrogen peroxide, hydrogen peroxide-liberating or—generating compounds, peroxyacids and their salts, and mixtures thereof. Preferably, the bleaching composition further comprises peroxyacid bleach precursors.

In yet another aspect, the present invention provides a detergent bleach composition comprising a peroxy bleaching compound and a catalyst as defined above, a surface-active material and a detergency builder.

Advantageously, complexes in accordance with the invention have been found to provide favourable stain removal in the presence of hydrogen peroxide or peroxyacids. Also, an improved bleaching activity has been noted, particularly in alkaline aqueous solutions containing peroxy compounds at concentrations generally present in the wash liquor during the fabric washing cycle. The complexes may also provide improved oxidation of organic substrates such as olefins, alcohols and unactivated hydrocarbons.

DETAILED DESCRIPTION OF THE INVENTION

Generally, the metal-complex catalyst of the invention may be used in a bleaching system comprising a peroxy compound, optionally together with a precursor therefor, and is suitable for use in the washing and bleaching of substrates including laundry, dishwashing and hard surface cleaning. Alternatively, the metal-complex catalyst of the invention may be used for bleaching in the textile, paper and woodpulp industries, as well as in waste water treatment.

As already stated, an advantage of the catalysts according to the present invention is that they exhibit a remarkably high oxidation activity in alkaline aqueous media in the presence of peroxy compounds.

A second advantage of the catalysts of the invention is that they can show good bleaching activity at a broader pH range (generally pH 6–11) than those observed for the previously disclosed iron complexes. Their performance was especially improved at a pH of around 10. This advantage may be particularly beneficial in view of the current detergent formulations that employ rather alkaline conditions, as well as the tendency to shift the pH during fabric washing from alkaline (typically, a pH of 10) to more neutral values. Furthermore, this advantage can be beneficial when using the present catalysts in machine dishwash formulations.

Another advantage is that the catalysts of the invention have a relatively low molecular weight and, consequently, are very weight-effective.

The active metal-complex catalysts of the present invention may be dosed as well-defined complexes. Alternatively, the catalysts may be formed in situ from suitable precursors for the catalyst, for example in a solution or dispersion containing the precursor materials. In one such example, the active catalyst may be formed in situ in a mixture comprising a salt of the metal M and the ligand L, or a ligand L-generating species, in a suitable solvent. Thus, for example, if M is iron, an iron salt such as $Fe(NO_3)_3$ can be mixed in solution with the ligand L, or a ligand L-generating species, to form the active metal complex. In another such example, the ligand L, or a ligand L-generating species, can be mixed with metal M ions present in the bleach or oxidation substrate or wash liquor to form the active catalyst in situ. Suitable ligand L-generating species include metal-free compounds or metal coordination complexes that comprise the ligand L and can be substituted by metal M ions to form the active metal complex according the formula (A).

Therefore, it will be appreciated that the catalyst in accordance with the present invention can be formed by any appropriate means, including in situ formation whereby precursors of the catalyst are transformed into the active metal complex of general formula (A) under conditions of storage or use. Preferably, the catalyst is formed as a well-defined complex or in a solvent mixture comprising a salt of the metal M and the ligand L or ligand L-generating species.

The ligand L, having the general formula $R^1R^1N$—W—$NR^1R^2$ as defined above, is a pentadentate ligand. By 'pentadentate' herein is meant that five hetero atoms can coordinate to the metal M ion in the metal-complex, of which two hetero atoms are linked by the bridging group W and one coordinating hetero atom is contained in each of the three $R^1$ groups. Preferably, the coordinating hetero atoms are nitrogen atoms.

The ligand L comprises at least one substituted heteroaryl group in each of the three $R^1$ groups. Preferably, the substituted heteroaryl group is a substituted pyridin-2-yl group, more preferably a methyl- or ethyl-substituted pyridin-2-yl group linked to an N atom in the above formula via a methylene group. More preferably, the substituted heteroaryl group is a 3-methyl-pyridin-2-yl group linked to an N atom via methylene. The group $R^2$ is a substituted or unsubstituted alkyl, aryl or arylalkyl group, provided that $R^2$ is different from each of the groups $R^1$ in the formula above. Suitable substituents are selected from hydroxy, alkoxy, carboxylate, carboxamide, carboxylic ester, sulphonate, amine, alkylamine and $N^+(R^4)_3$, wherein $R^4$ is selected from hydrogen, alkanyl, alkenyl, arylalkanyl, arylalkenyl, oxyalkanyl, oxyalkenyl, aminoalkanyl, aminoalkenyl, alkanyl ether and alkenyl ether. Preferably, $R^2$ is methyl, ethyl, benzyl, 2-hydroxyethyl or 2-methoxyethyl. More preferably, $R^2$ is methyl or ethyl.

The bridging group W may be a substituted or unsubstituted alkylene group selected from —$CH_2CH_2$—, —$CH_2CH_2CH_2$—, —$CH_2CH_2CH_2CH_2$—, and —$CH_2$—$C_6H_4$—$CH_2$— (wherein —$C_6H_4$— can be ortho-, para-, or meta-$C_6H_4$—). Preferably, the bridging group is an ethylene or 1,4-butylene group, more preferably an ethylene group.

Examples of preferred ligands in their simplest forms are:

N-methyl-N,N',N'-tris(3-methyl-pyridin-2-ylmethyl) ethylene-1,2-diamine;

N-ethyl-N,N',N'-tris(3-methyl-pyridin-2-ylmethyl)ethylene-1,2-diamine;

N-benzyl-N,N',N'-tris(3-methyl-pyridin-2-ylmethyl) ethylene-1,2-diamine;

N-(2-hydroxyethyl)-N,N',N'-tris(3-methyl-pyridin-2-ylmethyl)ethylene-1,2-diamine;

N-(2-methoxyethyl)-N,N',N'-tris(3-methyl-pyridin-2-ylmethyl)ethylene-1,2-diamine;

N-methyl-N,N',N'-tris(5-methyl-pyridin-2-ylmethyl) ethylene-1,2-diamine;

N-ethyl-N,N',N'-tris(5-methyl-pyridin-2-ylmethyl)ethylene-1,2-diamine;

N-benzyl-N,N',N'-tris(5-methyl-pyridin-2-ylmethyl) ethylene-1,2-diamine;

N-(2-hydroxyethyl)-N,N',N'-tris(5-methyl-pyridin-2-ylmethyl)ethylene-1,2-diamine;

N-(2-methoxyethyl)-N,N',N'-tris(5-methyl-pyridin-2-ylmethyl)ethylene-1,2-diamine;

N-methyl-N,N',N'-tris(3-ethyl-pyridin-2-ylmethyl)ethylene-1,2-diamine;

N-ethyl-N,N',N'-tris(3-ethyl-pyridin-2-ylmethyl)ethylene-1,2-diamine;

N-benzyl-N,N',N'-tris(3-ethyl-pyridin-2-ylmethyl)ethylene-1,2-diamine;

N-(2-hydroxyethyl)-N,N',N'-tris(3-ethyl-pyridin-2-ylmethyl)ethylene-1,2-diamine;

N-(2-methoxyethyl)-N,N',N'-tris(3-ethyl-pyridin-2-ylmethyl)ethylene-1,2-diamine;

N-methyl-N,N',N'-tris(5-ethyl-pyridin-2-ylmethyl)ethylene-1,2-diamine;

N-ethyl-N,N',N'-tris(5-ethyl-pyridin-2-ylmethyl)ethylene-1,2-diamine;

N-benzyl-N,N',N'-tris(5-ethyl-pyridin-2-ylmethyl)ethylene-1,2-diamine; and

N-(2-methoxyethyl)-N,N',N'-tris(5-ethyl-pyridin-2-ylmethyl)ethylene-1,2-diamine.

More preferred ligands are:

N-methyl-N,N',N'-tris(3-methyl-pyridin-2-ylmethyl) ethylene-1,2-diamine;

N-ethyl-N,N',N'-tris(3-methyl-pyridin-2-ylmethyl)ethylene-1,2-diamine;

N-benzyl-N,N',N'-tris(3-methyl-pyridin-2-ylmethyl) ethylene-1,2-diamine;

N-(2-hydroxyethyl)-N,N',N'-tris(3-methyl-pyridin-2-ylmethyl)ethylene-1,2-diamine; and N-(2-methoxyethyl)-N,N',N'-tris(3-methyl-pyridin-2-ylmethyl)ethylene-1,2-diamine.

The most preferred ligands are:

N-methyl-N,N',N'-tris(3-methyl-pyridin-2-ylmethyl) ethylene-1,2-diamine; and

N-ethyl-N,N',N'-tris(3-methyl-pyridin-2-ylmethyl)ethylene-1,2-diamine.

The metal-complex catalysts according to the invention may include suitable counter ions to balance the charge z on the complex formed by the ligand L, metal M and coordinating species X. Thus, if the charge z is positive, Y may be an anion such as $R^6COO^-$, $BPh_4^-$, $ClO_4^-$, $BF_4^-$, $PF_6^-$, $R^6SO_3^-$, $R^6SO_4^-$, $SO_4^{2-}$, $NO_3^-$, $F^-$, $Cl^-$, $Br^-$, or $I^-$, with $R^6$ being hydrogen, optionally substituted alkyl or optionally substituted aryl. If z is negative, Y may be a common cation such as an alkali metal, alkaline earth metal or (alkyl) ammonium cation.

Suitable counter ions Y include those which give rise to the formation of storage-stable solids. Preferred counter ions for the preferred metal complexes are selected from $R^6COO^-$, $ClO_4^-$, $BF_4^-$, $PF_6^-$, $R^6SO_3^-$ (in particular $CF_3SO_3^-$), $R^6SO_4^-$, $SO_4^{2-}$, $NO_3^-$, $F^-$, $Cl^-$, $Br^-$, and $I^-$ with $R^6$ being hydrogen, optionally substituted phenyl, naphthyl or $C_1$–$C_4$ alkyl.

Suitable coordinating species X may be selected from $R^5OH$, $NR^5_3$, $R^5CN$, $R^5OO^-$, $R^5S^-$, $R^5O^-$, $R^5COO^-$, $OCN^-$, $SCN^-$, $N_3^-$, $CN^-$, $F^-$, $Cl^-$, $Br^-$, $I^-$, $O^{2-}$, $O_2^{2-}$, $O_2^-$, $NO_3^-$, $NO_2^-$, $SO_4^{2-}$, $SO_3^{2-}$, $PO_4^{3-}$ and aromatic N donors selected from pyridines, pyrazines, pyrazoles, imidazoles, benzimidazoles, pyrimidines, triazoles and thiazoles, with $R^5$ being selected from hydrogen, optionally substituted alkyl and optionally substituted aryl. X may also be the species $LMO^-$ or $LMOO^-$, wherein M is a transition metal and L is a ligand as defined above. Preferred coordinating species X are $CH_3CN$, $H_2O$, $F^-$, $Cl^-$, $Br^-$, $OOH^-$, $O_2^{2-}$, $O_2^-$, $LMO^-$, $LMOO^-$, $R^5COO^-$ and $R^5O^-$ wherein $R^5$ represents hydrogen or optionally substituted phenyl, naphthyl, or $C_1$–$C_4$ alkyl.

The effective level of the metal-complex catalyst, expressed in terms of parts per million (ppm) of metal M in an aqueous bleaching solution, will normally range from 0.001 ppm to 100 ppm, preferably from 0.01 ppm to 20 ppm, most preferably from 0.1 ppm to 10 ppm. Higher levels may be desired and applied in industrial bleaching processes, such as textile and paper pulp bleaching. The lower range levels are preferably used in domestic laundry operations.

The metal M may be selected from iron (Fe), manganese (Mn) and copper (Cu). Preferably, the metal is Fe or Mn, and more preferably Fe.

The Peroxy Bleaching Compound

The peroxy bleaching compound may be any compound which is capable of yielding hydrogen peroxide in aqueous solution, including hydrogen peroxide and hydrogen peroxide adducts. Hydrogen peroxide sources are well known in the art. They include the alkali metal peroxides, organic peroxides such as urea peroxide, and inorganic persalts, such as the alkali metal perborates, percarbonates, perphosphates, persilicates and persulphates. Mixtures of two or more such compounds may also be suitable.

Particularly preferred are sodium perborate tetrahydrate and, especially, sodium perborate monohydrate. Sodium perborate monohydrate is preferred because of its high active oxygen content. Sodium percarbonate may also be preferred for environmental reasons. The amount thereof in the composition of the invention usually will be within the range of about 2 to 35% by weight, preferably from 10 to 25% by weight.

Another suitable hydrogen peroxide generating system is a combination of a $C_1$–$C_4$ alkanol oxidase and a $C_1$–$C_4$ alkanol, especially a combination of methanol oxidase (MOX) and ethanol. Such combinations are disclosed in WO-A-9507972, which is incorporated herein by reference. A further suitable hydrogen peroxide generating system uses a combination of glucose oxidase and glucose.

Alkylhydroxy peroxides are another class of suitable peroxy bleaching compounds. Examples of these materials include cumene hydroperoxide and t-butyl hydroperoxide.

Organic peroxyacids are also suitable as peroxy bleaching compounds. Such materials normally have the general formula:

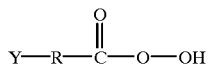

wherein R is an alkylene or alkyl- or alkylidene-substituted alkylene group containing from 1 to about 20 carbon atoms, optionally having an internal amide linkage; or a phenylene or substituted phenylene group; and Y is hydrogen, halogen, alkyl, aryl, an imido-aromatic or non-aromatic group, a —COOH or —COOOH group or a quaternary ammonium group.

Typical monoperoxyacids useful herein include, for example:

(i) peroxybenzoic acid and ring-substituted peroxybenzoic acids, e.g. peroxy-α-naphthoic acid;

(ii) aliphatic, substituted aliphatic and arylalkyl monoperoxyacids, e.g. peroxylauric acid, peroxystearic acid and N,N-phthaloylaminoperoxy caproic acid (PAP); and (iii) 6-octylamino-6-oxo-peroxyhexanoic acid.

Typical diperoxyacids useful herein include, for example:

(iv) 1,12-diperoxydodecanedioic acid (DPDA);

(v) 1,9-diperoxyazelaic acid;

(vi) diperoxybrassylic acid; diperoxysebacic acid and diperoxyisophthalic acid;

(vii) 2-decyldiperoxybutane-1,4-dioic acid; and (viii) 4,4'-sulphonylbisperoxybenzoic acid.

Also suitable are inorganic peroxyacid compounds such as, for example, potassium monopersulphate (MPS). If organic or inorganic peroxyacids are used as the peroxygen compound, the amount thereof will normally be within the range of about 2 to 10% by weight, preferably from 4 to 8% by weight.

Generally, the bleaching composition of the invention can be suitably formulated to contain from 2 to 35%, preferably from 5 to 25% by weight, of the peroxy bleaching compound.

All these peroxy compounds may be utilized either alone or in conjunction with a peroxyacid bleach precursor and/or an organic bleach catalyst not containing a transition metal.

Peroxyacid bleach precursors are known and amply described in literature, such as in the GB-A-0,836,988; GB-A-0,864,798; GB-A-0,907,356; GB-A-1,003,310 and GB-A-1,519,351; DE-A-3,337,921; EP-A-0,185,522; EP-A-0,174,132; EP-A-0,120,591; and U.S. Pat. No. 1,246,339; U.S. Pat. No. 3,332,882; U.S. Pat. No. 4,128,494; U.S. Pat. No. 4,412,934 and U.S. Pat. No. 4,675,393.

Another useful class of peroxyacid bleach precursors is that of the cationic i.e. quaternary ammonium substituted peroxyacid precursors as disclosed in U.S. Pat. No. 4,751,015 and U.S. Pat. No. 4,397,757, in EP-A-0,284,292 and EP-A-0,331,229. Examples of peroxyacid bleach precursors of this class are:

2-(N,N,N-trimethyl ammonium)ethyl sodium-4-sulphophenyl carbonate chloride—(SPCC);

N-octyl-N,N-dimethyl-$N_{10}$-carbophenoxy decyl ammonium chloride—(ODC);

3-(N,N,N-trimethyl ammonium) propyl sodium-4-sulphophenyl carboxylate; and

N,N,N-trimethyl ammonium toluyloxy benzene sulphonate.

A further special class of bleach precursors is formed by the cationic nitriles as disclosed in EP-A-0,303,520; EP-A-0,458,396 and EP-A-0,464,880.

Any one of these peroxyacid bleach precursors can be used in the present invention, though some may be more preferred than others. Of the above classes of bleach precursors, the preferred classes are the esters, including acyl phenol sulphonates and acyl alkyl phenol sulphonates; the acyl-amides; and the quaternary ammonium substituted peroxyacid precursors including the cationic nitriles.

Examples of the preferred peroxyacid bleach precursors or activators are sodium-4-benzoyloxy benzene sulphonate (SBOBS); N,N,N'N'-tetraacetyl ethylene diamine (TAED); sodium-1-methyl-2-benzoyloxy benzene-4-sulphonate; sodium-4-methyl-3-benzoyloxy benzoate; 2-(N,N,N-trimethyl ammonium)ethyl sodium-4-sulphophenyl carbonate chloride (SPCC); trimethyl ammonium toluyloxy-benzene sulphonate; sodium nonanoyloxybenzene sulphonate (SNOBS); sodium 3,5,5-trimethyl hexanoyl-oxybenzene sulphonate (STHOBS); and the substituted cationic nitriles.

The precursors may be used in an amount of up to 12%, preferably from 2 to 10% by weight, of the composition.

The Detergent Bleach Composition

The bleaching composition of the invention has particular application in detergent formulations. Accordingly, in another aspect, the invention provides a detergent bleach composition comprising a peroxy bleaching compound as defined above, the aforesaid metal-complex catalyst having the general formula (A), a surface-active material and a detergency builder.

The metal-complex catalyst will be present in the detergent bleach composition of the invention in amounts so as to provide the required level in the wash liquor. Generally, the metal-complex catalyst level in the detergent bleach composition corresponds to an iron, manganese or copper content of from 0.0005% to 0.5% by weight. When the dosage of detergent bleach composition is relatively low, e.g. about 1 to 2 g/l, the metal content in the formulation is suitably 0.0025 to 0.5%, preferably 0.005 to 0.25% by weight. At higher product dosages, as used for example by European consumers, the metal content in the formulation is suitably 0.0005 to 0.1%, preferably 0.001 to 0.05% by weight.

Detergent bleach compositions of the invention are effective over a wide pH-range of between 7 and 13, with optimal pH-range lying between 8 and 11.

The Surface-Active Material

The detergent bleach composition according to the present invention generally contains a surface-active material in an amount of from 10 to 50% by weight. The surface-active material may be naturally derived, such as soap, or a synthetic material selected from anionic, nonionic, amphoteric, zwitterionic, cationic actives and mixtures thereof. Many suitable actives are commercially available and are fully described in the literature, for example in "Surface Active Agents and Detergents", Volumes I and II, by Schwartz, Perry and Berch.

Typical synthetic anionic surface-actives are usually water-soluble alkali metal salts of organic sulphates and sulphonates having alkyl radicals containing from about 8 to about 22 carbon atoms, the term alkyl being used to include the alkyl portion of higher aryl radicals. Examples of suitable synthetic anionic detergent compounds are sodium and ammonium alkyl sulphates, especially those obtained by sulphating higher ($C_8$–$C_{18}$) alcohols produced, for example, from tallow or coconut oil; sodium and ammonium alkyl ($C_9$–$C_{20}$) benzene sulphonates, particularly sodium linear secondary alkyl ($C_{10}$–$C_{15}$) benzene sulphonates; sodium alkyl glyceryl ether sulphates, especially those ethers of the higher alcohols derived from tallow or coconut oil fatty acid monoglyceride sulphates and sulphonates; sodium and ammonium salts of sulphuric acid esters of higher ($C_9$–$C_{18}$) fatty alcohol alkylene oxide, particularly ethylene oxide, reaction products; the reaction products of fatty acids such as coconut fatty acids esterified with isethionic acid and neutralised with sodium hydroxide; sodium and ammonium salts of fatty acid amides of methyl taurine; alkane mono-sulphonates such as those derived by reacting alpha-olefins ($C_8$–$C_{20}$) with sodium bisulphite and those derived by reacting paraffins with $SO_2$ and $Cl_2$ and then hydrolysing with a base to produce a random sulphonate; sodium and ammonium ($C_7$–$C_{12}$) dialkyl sulphosuccinates; and olefin sulphonates, which term is used to describe material made by reacting olefins, particularly ($C_{10}$–$C_{20}$) alpha-olefins, with $SO_3$ and then neutralising and hydrolysing the reaction product. The preferred anionic detergent compounds are sodium ($C_{10}$–$C_{15}$) alkylbenzene sulphonates, and sodium ($C_{16}$–$C_{18}$) alkyl ether sulphates.

Examples of suitable nonionic surface-active compounds which may be used, preferably together with the anionic surface-active compounds, include, in particular, the reaction products of alkylene oxides, usually ethylene oxide, with alkyl ($C_6$–$C_{22}$) phenols, generally 5–25 EO, i.e. 5–25 units of ethylene oxides per molecule; and the condensation products of aliphatic ($C_8$–$C_{18}$) primary or secondary linear or branched alcohols with ethylene oxide, generally 2–30 EO. Other so-called nonionic surface-actives include alkyl polyglycosides, sugar esters, long-chain tertiary amine oxides, long-chain tertiary phosphine oxides and dialkyl sulphoxides.

Amphoteric or zwitterionic surface-active compounds can also be used in the compositions of the invention but this is not normally desired owing to their relatively high cost. If any amphoteric or zwitterionic detergent compounds are used, it is generally in small amounts in compositions based on the much more commonly used synthetic anionic and nonionic actives.

The detergent bleach composition of the invention will preferably comprise from 1 to 15% wt of anionic surfactant and from 10 to 40% by weight of nonionic surfactant. In a further preferred embodiment, the detergent active system is free from $C_{16}$–$C_{12}$ fatty acid soaps.

The Detergency Builder

The detergent bleach composition of the invention normally and preferably also contains a detergency builder in an amount of from about 5 to 80% by weight, preferably from about 10 to 60% by weight.

Builder materials may be selected from 1) calcium sequestrant materials, 2) precipitating materials, 3) calcium ion-exchange materials and 4) mixtures thereof.

Examples of calcium sequestrant builder materials include alkali metal polyphosphates, such as sodium tripolyphosphate; nitrilotriacetic acid and its water-soluble salts; the alkali metal salts of carboxymethyloxy succinic acid, ethylene diamine tetraacetic acid, oxydisuccinic acid, mellitic acid, benzene polycarboxylic acids, citric acid; and polyacetal carboxylates as disclosed in U.S. Pat. No. 4,144,226 and U.S. Pat. No. 4,146,495.

Examples of precipitating builder materials include sodium orthophosphate and sodium carbonate.

Examples of calcium ion-exchange builder materials include the various types of water-insoluble crystalline or amorphous aluminosilicates, of which zeolites are the best known representatives, e.g. zeolite A, zeolite B (also known as zeolite P), zeolite C, zeolite X, zeolite Y and also the zeolite P-type as described in EP-A-0,384,070.

In particular, the compositions of the invention may contain any one of the organic and inorganic builder materials, though, for environmental reasons, phosphate builders are preferably omitted or only used in very small amounts. Typical builders usable in the present invention are, for example, sodium carbonate, calcite/carbonate, the sodium salt of nitrilotriacetic acid, sodium citrate, carboxymethyloxy malonate, carboxymethyloxy succinate and water-insoluble crystalline or amorphous aluminosilicate builder materials, each of which can be used as the main builder, either alone or in admixture with minor amounts of other builders or polymers as co-builder.

It is preferred that the composition contains not more than 5% by weight of a carbonate builder, expressed as sodium carbonate, more preferably not more than 2.5% by weight to substantially nil, if the composition pH lies in the lower alkaline region of up to 10.

Other Ingredients

Apart from the components already mentioned, the detergent bleach composition of the invention can contain any of the conventional additives in amounts of which such materials are normally employed in fabric washing detergent compositions. Examples of these additives include buffers such as carbonates, lather boosters, such as alkanolamides, particularly the monoethanol amides derived from palmkernel fatty acids and coconut fatty acids; lather depressants, such as alkyl phosphates and silicones; anti-redeposition agents, such as sodium carboxymethyl cellulose and alkyl or substituted alkyl cellulose ethers; stabilizers, such as phosphonic acid derivatives (i.e. Dequest® types); fabric softening agents; inorganic salts and alkaline buffering agents, such as sodium sulphate and sodium silicate; and, usually in very small amounts, fluorescent agents; perfumes; enzymes, such as proteases, cellulases, lipases, amylases and oxidases; germicides and colourants.

When using a hydrogen peroxide source, such as sodium perborate or sodium percarbonate, as the bleaching compound, it is preferred that the composition contains not more than 5% by weight of a carbonate buffer, expressed as sodium carbonate, more preferable not more than 2.5% by weight to substantially nil, if the composition pH lies in the lower alkaline region of up to 10.

Of the additives, transition metal sequestrants such as EDTA, and phosphonic acid derivatives such as EDTMP (ethylene diamine tetra(methylene phosphonate)) are of special importance, as not only do they improve the stability of the catalyst/$H_2O_2$ system and sensitive ingredients, such as enzymes, fluorescent agents, perfumes and the like, but also improve the bleach performance, especially at the higher pH region of above 10, particularly at pH 10.5 and above.

The invention will now be further illustrated by way of the following non-limiting examples:

EXAMPLES

Synthesis

All reactions were performed under a nitrogen atmosphere, unless indicated otherwise. All reagents and solvents were obtained from Aldrich or Across and used as received, unless stated otherwise. Petroleum ether 40–60 was distilled using a rotavapor before using it as eluent. Flash column chromatography was performed using Merck silica gel 60 or aluminium oxide 90 (activity II–III according to Brockmann). $^1$H NMR (300 MHz) and $^{13}$C NMR (75 MHz) were recorded in $CDCl_3$, unless stated otherwise. Multiplicities were addressed with the normal abbreviations using p for quintet.

Synthesis of Starting Materials for Ligand Synthesis

Synthesis of N-benzyl amino acetonitrile. N-benzyl amine (5.35 g, 50 mmol) was dissolved in a water:methanol mixture (50 mL, 1:4). Hydrochloric acid (aq., 30%) was added until the pH reached 7.0. Added was NaCN (2.45 g, 50 mmol). After cooling to 0° C., formaline (aq. 35%, 4.00 g, 50 mmol) was added. The reaction was followed by TLC (aluminium oxide; EtOAc:$Et_3$N=9:1) until benzylamine could be detected. Subsequently the methanol was evaporated in vacuo and the remaining oil "dissolved" in water. The aqueous phase was extracted with methylene chloride (3×50 mL). The organic layers were collected and the solvent removed in vacuo. The residue was purified by Kugelrohr distillation (p=20 mm Hg, T=120° C.) giving N-benzyl amino acetonitrile (4.39 g, 30 mmol. 60%) as a colourless oil.

$^1$H NMR: δ 7.37–7.30 (m, 5H), 3.94 (s, 2H), 3.57 (s, 2H), 1.67 (br s, 1H);

$^{13}$C NMR: δ 137.74, 128.58, 128.46, 128.37, 127.98, 127.62, 117.60, 52.24, 36.19.

Synthesis of N-ethyl amino acetonitrile. This synthesis was performed analogously to the synthesis reported for N-benzyl amino acetonitrile. However, detection was done by dipping the TLC plate in a solution of $KMnO_4$ and heating the plate until bright spots appeared. Starting from ethylamine (2.25 g, 50 mmol), pure N-ethyl amino acetonitrile (0.68 g, 8.1 mmol, 16%) was obtained as a slightly yellow oil.

$^1$H NMR: δ 3.60 (s, 2H), 2.78 (q, J=7.1, 2H), 1.22 (br s, 1H), 1.14 (t, J=7.2, 3H);

$^{13}$C NMR: δ 117.78, 43.08, 37.01, 14.53.

Synthesis of N-ethyl ethylene-1,2-diamine. The synthesis was performed according to Hageman; J. Org. Chem.; 14; 1949; 616, 634, starting from N-ethyl amino acetonitrile.

Synthesis of N-benzyl ethylene-1,2-diamine. Sodium hydroxide (890 mg; 22.4 mmol) was dissolved in ethanol (96%, 20 mL), the process taking the better part of 2 hours. Added was N-benzyl amino acetonitrile (4, 2.92 g, 20 mmol) and Raney Nickel (approx. 0.5 g). Hydrogen pressure was applied (p=3.0 atm.) until hydrogen uptake ceased. The mixture was filtered over Cellite, washing the residue with ethanol. The filter should not run dry since Raney Nickel is relatively pyrophoric. The Cellite containing the Raney Nickel was destroyed by putting the mixture in dilute acid, causing gas formation). The ethanol was evaporated in in vacuo and the residue dissolved in water. Upon addition of base (aq. NaOH, 5N) the product oiled out and was extracted with chloroform (3×20 mL). After evaporation of the solvent in vacuo the $^1$H NMR showed the presence of benzylamine. Separation was enforced by column chromatography (silica gel; MeOH: EtOAc:$Et_3$N=1:8:1) yielding the benzyl amine, followed by the solvent mixture MeOH; EtOAc:$Et_3$N=5:4:1. Detection was done by using aluminium oxide as a solid phase in TLC, yielding pure N-benzyl ethylene-1,2-diamine (2.04 g, 13.6 mmol, 69%).

$^1$H NMR: δ 7.33–7.24 (m, 5H), 3.80 (s, 2H), 2.82 (t, J=5.7, 2H), 2.69 (t, J=5.7, 2H), 1.46 (br s, 3H);

$^{13}$C NMR: δ 140.37, 128.22, 127.93, 126.73, 53.73, 51.88. 41.66.

Synthesis of 2-acetoxymethyl-5-methyl pyridine. 2,5-Lutidine (31.0 g, 290 mmol), acetic acid (180 mL) and hydrogen peroxide (30 mL, 30%) were heated at 70–80° C. for 3 hours. Hydrogen peroxide (24 mL, 30%) was added and the subsequent mixture heated for 16 hours at 60–70 ° C. Most of the mixture of (probably) hydrogen peroxide, water, acetic acid, and peracetic acid was removed in vacuo (rotavap, water bath 50° C. until p=20 mbar). The resulting mixture containing the N-oxide was added dropwise to acetic anhydride heated under reflux. This reaction was highly exothermic, and was controlled by the dropping speed. After heating under reflux for an hour, methanol was added dropwise. This reaction was highly exothermic. The resulting mixture was heated under reflux for another 30 minutes. After evaporation of the methanol (rotavap, 50° C. until p=20 mbar), the resulting mixture was purified by Kugelrohr distillation (p=20 mm Hg, T=150° C.). The clear oil that was obtained still contained acetic acid. This was removed by extraction ($CH_2Cl_2$, $NaHCO_3$ (sat.)) yielding the pure acetate of 2-acetoxymethyl-5-methyl pyridine (34.35 g, 208 mmol, 72%) as a slightly yellow oil.

$^1$H NMR: δ 8.43 (s, 1H), 7.52 (dd, J=7.8, J=1.7, 1H), 7.26 (d, J=7.2, 1H), 5.18 (s, 2H), 2.34 (s, 3H), 2.15 (s, 3H);

$^{13}$C NMR: δ 170.09, 152.32, 149.39, 136.74, 131.98, 121.14, 66.31, 20.39, 17.66.

Synthesis of 2-acetoxymethyl-5-ethyl pyridine. This synthesis was performed analogously to the synthesis reported for 2-acetoxymethyl-5-methyl pyridine. Starting from 5-ethyl-2-methyl pyridine (35.10 g, 290 mmol), pure 2-acetoxymethyl-5-ethyl pyridine (46.19 g, 258 mmol, 89%) was obtained as a slightly yellow oil.

$^1$H NMR: δ 8.47 (s, 1H), 7.55 (d, J=7.8, 1H), 7.29 (d, J=8.1, 1H), 2.67 (q, J=7.8, 2H), 2.14 (s, 3H), 1.26 (t, J=7.77, 3H);

$^3$C NMR: δ 170.56, 152.80, 149.11, 138.47, 135.89, 121.67, 66.72, 25.65, 20.78, 15.13.

Synthesis of 2-acetoxymethyl-3-methyl pyridine. This synthesis was performed analogously to the synthesis reported for 2-acetoxymethyl-5-methyl pyridine. The only difference was the reversal of the Kugelrohr distillation and the extraction. According to $^1$H NMR a mixture of the acetate and the corresponding alcohol was obtained. Starting from 2,3-picoline (31.0 g, 290 mmol), pure 2-acetoxymethyl-3-methyl pyridine (46.19 g, 258 mmol, 89%, calculated for pure acetate) was obtained as a slightly yellow oil.

$^1$H NMR: δ 8.45 (d, J=3.9, 1H), 7.50 (d, J=8.4, 1H), 7.17 (dd, J=7.8, J=4.8, 1H), 5.24 (s, 2H), 2.37 (s, 3H), 2.14 (s, 3H).

Synthesis of 2-hydroxymethyl-5-methyl pyridine. 2-Acetoxymethyl-5-methyl pyridine (30 g, 182 mmol) was dissolved in hydrochloric acid (100 mL, 4 N). The mixture was heated under reflux, until TLC (silica gel; triethylamine:ethyl acetate:petroleum ether 40–60=1:9:19) showed complete absence of the acetate (normally 1 hour). The mixture was cooled, brought to pH>11, extracted with dichloromethane (3×50 mL) and the solvent removed in vacuo. Pure 2-hydroxymethyl-5-methyl pyridine (18.80 g, 152 mmol, 84%) was obtained by Kugelrohr distillation (p=20 mm Hg, T=130° C.) as a slightly yellow oil.

$^1$H NMR: δ 8.39 (s, 1H), 7.50 (dd, J=7.8, J=1.8, 1H), 7.15 (d, J=8.1, 1H), 4.73 (s, 2H), 3.83 (br s, 1H), 2.34 (s, 3H);

$^{13}$C NMR: δ 156.67, 148.66, 137.32, 131.62, 120.24, 64.12, 17.98.

Synthesis of 2-hydroxymethyl-5-ethyl pyridine. This synthesis was performed analogously to the synthesis reported for 2-hydroxymethyl-5-methyl pyridine. Starting from 2-acetoxymethyl-5-ethyl pyridine (40 g, 223 mmol), pure 2-hydroxymethyl-5-ethyl pyridine (26.02 g, 189 mmol, 85%) was obtained as a slightly yellow oil.

$^1$H NMR: δ 8.40 (d, J=1.2, 1H), 7.52 (dd, J=8.0, J=2.0, 1H), 7.18 (d, J=8.1, 1H), 4.74 (s, 2H), 3.93 (br s, 1H), 2.66 (q, J=7.6, 2H), 1.26 (t, J=7.5, 3H);

$^{13}$C NMR: δ 156.67, 148.00, 137.87, 136.13, 120.27, 64.07, 25.67, 15.28.

Synthesis of 2-hydroxymethyl-3-methyl pyridine. This synthesis was performed analogously to the synthesis reported for 2-hydroxymethyl-5-methyl pyridine. Starting from 2-acetoxymethyl-3-methyl pyridine (25 g (recalculated for the mixture), 152 mmol), pure 2-hydroxymethyl-3-methyl pyridine (15.51 g, 126 mmol, 83%) was obtained as a slightly yellow oil.

$^1$H NMR: δ 8.40 (d, J=4.5, 1H)), 7.47 (d, J=7.2, 1H), 7.15 (dd, J=7.5, J=5.1, 1H), 4.85 (br s, 1H), 4.69 (s, 1H), 2.22 (s, 3H);

$^{13}$C NMR: δ 156.06, 144.97, 137.38, 129.53, 121.91, 61.38, 16.30.

Synthesis of Ligands

Synthesis of N-methyl-N,N',N'-tris(pyridin-2-ylmethyl) ethylene-1,2-diamine (L1). The ligand L1 (comparative) was prepared according to Bernal, Ivan; Jensen, Inge Margrethe; Jensen, Kenneth B.; McKenzie, Christine J.; Toftlund, Hans; Tuchagues, Jean-Pierre; J. Chem. Soc. Dalton Trans.; 22; 1995; 3667–3676.

Synthesis of N-methyl-N,N',N'-tris(3-methylpyridin-2-ylmethyl)ethylene-1,2-diamine (L2, Me-TRILEN). 2-Hydroxymethyl-3-methyl pyridine (5.00 g, 40.7 mmol) was dissolved in dichloromethane (30 mL). Thionyl chloride (30 mL) was added dropwise under cooling (ice bath). The resulting mixture was stirred for 1 hour and the solvents removed in vacuo (rotavap, until p=20 mm Hg, T=50° C.). To the resultant mixture was added dichloromethane (25 mL). Subsequently NaOH (5 N, aq.) was added dropwise until the pH (aqua)≧11. The reaction was quite vigorous in the beginning, since part of the thionyl chloride was still present. N-methyl ethylene-1,2-diamine (502 mg, 6.8 mmol) and additional NaOH (5 N, 10 mL) were added. The reaction mixture was stirred at room temperature for 45 hours. The mixture was poured into water (200 mL), and the pH checked (≧14, otherwise addition of NaOH (aq. 5N)). The reaction mixture was extracted with dichloromethane (3 or 4×50 mL, until no product could be detected by TLC). The combined organic phases were dried and the solvent removed in vacuo. Purification was enforced as described before, yielding N-methyl-N,N',N'-tris(3-methylpyridin-2-ylmethyl)ethylene-1,2-diamine as a slightly yellow oil. Purification was enforced by column chromatography (aluminium oxide 90 (activity II–III according to Brockmann); triethylamine:ethyl acetate:petroleum ether 40–60=1:9: 10) until the impurities were removed according to TLC (aluminium oxide, same eluent, Rf≈0.9). The compound was eluted using ethylacetate:triethyl amine=9:1. N-methyl-N,N',N'-tris(3-methylpyridin-2-ylmethyl) ethylene-1,2-diamine (L2, 1.743 g, 4.30 mmol, 63%) was obtained.

$^1$H NMR: δ 8.36 (d, J=3.0, 3H), 7.40–7.37 (m, 3H), 7.11–7.06 (m, 3H), 3.76 (s, 4H), 3.48 (s, 2H), 2.76–2.71 (m, 2H), 2.53–2.48 (m, 2H), 2.30 (s, 3H), 2.12 (s, 6H), (s, 3H);

$^{13}$C NMR: δ 156.82, 156.77, 145.83, 145.67, 137.61, 133.14, 132.72, 122.10, 121.88, 62.32, 59.73, 55.19, 51.87, 42.37, 18.22, 17.80.

Synthesis of N-ethyl-N,N',N'-tris(3-methylpyridin-2-ylmethyl)ethylene-1,2-diamine (L3, Et-TRILEN). This synthesis is performed analogously to the synthesis for L2.

Starting from 2-hydroxymethyl-3-methyl pyridine (25.00 g, 203 mmol) and N-ethyl ethylene-1,2-diamine (2.99 g, 34.0 mmol), N-ethyl-N,N',N'-tris(methylpyridin-2-ylmethyl) ethylene-1,2-diamine (L3, 11.49 g, 28.5 mmol, 84%) was obtained. Column chromatography (aluminium oxide; Et$_3$N:EtOAc:petroleum ether 40–60=1:9:30, followed by Et$_3$N:EtOAc=1:9).

$^1$H NMR: δ 8.34–8.30 (m, 3H), 7.40–7.34 (m, 3H), 7.09–7.03 (m, 3H), 3.71 (s, 4H), 3.58 (s, 2H), 2.64–2.59 (m, 2H), 2.52–2.47 (m, 2H), 2.43–2.36 (m, 2H), 2.31 (s, 3H), 2.10 (s, 6H), 0.87 (t, J=7.2, 3H);

$^{13}$C NMR: δ 157.35, 156.92, 145.65, 137.61, 133.14, 132.97, 122.09, 121.85, 59.81, 59.28, 51.98, 50.75, 48.02, 18.27, 17.80, 11.36.

Synthesis of N-benzyl-N,N',N'-tris(3-methylpyridin-2-ylmethyl)ethylene-1,2-diamine (L4, Bn-TRILEN). This synthesis is performed analogously to the synthesis for L2. Starting from 2-hydroxymethyl-3-methylpyridine (3.00 g 24.4 mmol), and N-benzyl ethylene-1,2-diamine (610 mg, 4.07 mmol), N-benzyl-N,N',N'-tris(3-methylpyridin-2-ylmethyl)ethylene-1,2-diamine (L4, 1.363 g, 2.93 mmol, 72%) was obtained. Column chromatography (aluminium oxide; Et$_3$N:EtOAc:petroleum ether 40–60=1:9:10).

$^1$H NMR: δ 8.33–8.29 (m, 3H), 7.37–7.33 (m, 3H), 7.21–7.03 (m, 8H), 3.66 (s, 4H), 3.60 (s, 2H), 3.42 (s, 2H), 2.72–2.67 (m, 2H), 2.50–2.45 (m, 2H), 2.23 (s, 3H), 2.03 (s, 6H);

$^{13}$C NMR: δ 157.17, 156.96, 145.83, 145.78, 139.29, 137.91, 137.80, 133.45, 133.30, 128.98, 127.85, 126.62, 122.28, 122.22, 59.99, 58.83, 51.92, 51.54, 18.40, 17.95.

Synthesis of N-hydroxyethyl-N,N',N'-tris(3-methylpyridin-2-ylmethyl)ethylene-1,2-diamine (L5). This synthesis is performed analogously to the synthesis for L6. Starting from 2-hydroxymethyl-3-methyl pyridine (3.49 g, 28.4 mmol), and N-hydroxyethyl ethylene-1,2-diamine (656 mg 6.30 mmol), after 7 days N-hydroxyethyl-N,N',N'-tris (3-methylpyridin-2-ylmethyl)ethylene-1,2-diamine (L5, 379 mg, 0.97 mmol, 14%) was obtained.

$^1$H NMR: δ 8.31–8.28 (m, 3H), 7.35–7.33 (m, 3H), 7.06–7.00 (m, 3H), 4.71 (br s, 1H), 3.73 (s, 4H), 3.61 (s, 2H), 3.44 (t, J=5.1, 2H), 2.68 (s, 2H), 2.57 (t, J=5.0, 2H), 2.19 (s, 3H), 2.10 (s, 6H);

$^{13}$C NMR: δ 157.01, 156.88, 145.91, 145.80, 137.90, 137.83, 133.30, 131.89, 122.30, 121.97, 59.60, 59.39, 57.95, 56.67, 51.95, 51.22, 18.14, 17.95.

Synthesis of N-methyl-N,N',N'-tris(5-methylpyridin-2-ylmethyl)ethylene-1,2-diamine (L6). 2-hydroxymethyl-5-methyl pyridine (2.70 g, 21.9 mmol) was dissolved in dichloromethane (25 mL). Thionyl chloride (25 mL) was added dropwise under cooling (ice bath). The resulting mixture was stirred for 1 hour and the solvents removed in vacuo (rotavap, until p=20 mm Hg, T±35° C.). The remaining oil was used directly in the synthesis of the ligands, since it was known from the literature that the free picolyl chlorides are somewhat unstable and are highly lachrymatory. To the resultant mixture was added dichloromethane (25 mL) and N-methyl ethylene-1,2-diamine (360 mg, 4.86 mmol). Subsequently NaOH (5 N, aq.) was added dropwise. The reaction was quite vigorous in the beginning, since part of the thionyl chloride was still present. The aqueous layer was brought to pH=10, and additional NaOH (5 N, 4.38 mL) was added. The reaction mixture was stirred until a sample indicated complete conversion (7 days). The reaction mixture was extracted with dichloromethane (3×25 mL). The combined organic phases were dried and the solvent removed in vacuo. Purification was enforced by column chromatography (aluminium oxide 90 (activity II–III according to Brockmann); triethylamine:ethyl acetate:petroleum ether 40–60=1:9:10) until the impurities were removed according to TLC (aluminium oxide, same eluent, Rf≈0.9). The compound was eluted using ethyl acetate:triethyl amine=9:1, yielding N-methyl-N,N',N'-tris(5-methylpyridin-2-ylmethyl)ethylene-1,2-diamine (L6, 685 mg, 1.76 mmol, 36%) as a slightly yellow oil.

$^1$H NMR: δ 8.31 (s, 3H) 7.43–7.35 (m, 5H), 7.21 (d, J=7.8. 1H), 3.76 (s, 4H), 3.56 (s, 2H), 2.74–2.69 (m, 2H), 2.63–2.58 (m, 2H), 2.27 (s, 6H), 2.16 (s, 3H);

$^{13}$C NMR: δ 156.83, 156.43, 149.23, 149.18, 136.85, 136.81, 131.02, 122.41, 122.30, 63.83, 60.38, 55.53, 52.00, 42.76, 18.03.

Synthesis of N-methyl-N,N',N'-tris(5-ethylpyridin-2-ylmethyl)ethylene-1,2-diamine (L7). This synthesis is performed analogously to the synthesis for L6. Starting from 2-hydroxymethyl-5-ethyl pyridine (3.00 g, 21.9 mmol), and N-methyl ethylene-1,2-diamine (360 mg, 4.86 mmol), after 7 days N-methyl-N,N',N'-tris(5-ethylpyridin-2-ylmethyl) ethylene-1,2-diamine (L7, 545 mg, 1.26 mmol, 26%) was obtained.

$^1$H NMR: δ 8.34 (s, 3H), 7.44–7.39 (m, 5H), 7.26 (d, J=6.6, 1H), 3.80 (s, 4H), 3.59 (s, 2H), 2.77–2.72 (m, 2H), 2.66–2.57 (m, 8H), 2.18 (s, 3H), 1.23 (t,J=7.5, 9H);

$^{13}$C NMR: δ 157.14, 156.70, 148.60, 148.53, 137.25, 135.70, 122.59, 122.43, 63.91, 60.48, 55.65, 52.11, 42.82, 25.73, 15.36.

Synthesis of Metal-Ligand Complexes

Synthesis of N-methyl-N,N',N'-tris(3-methylpyridin-2-ylmethyl)ethylene-1,2-diamine iron(II)chloride.PF$_6$ ([L2 Fe(II)Cl]PF$_6$). FeCl$_2$.4H$_2$O (51.2 mg,257 μmol) was dissolved in MeOH:H$_2$O=1:1 (2.5 mL). The solution was heated to 50° C. Added was N-methyl-N,N',N'-tris(3-methylpyridin-2-ylmethyl)ethylene-1,2-diarnine (L2, 100 mg, 257 μmol) in MeOH:H$_2$O=1:1 (2.0 mL). Subsequently NaPF$_6$ (86.4 mg, 514 μmol) in H$_2$O (2.5 mL) was added dropwise. Cooling to room temperature, filtration and drying in vacuo (p=0.05 mm Hg, T=room temperature) yielded the complex [L2 Fe(II)Cl]PF$_6$ (149 mg, 239 μmol, 93%) as a yellow solid.

$^1$H NMR (CD$_3$CN, paramagnetic): δ 167.17, 142.18, 117.01, 113.34, 104.79, 98.62, 70.77, 67.04, 66.63, 58.86, 57.56, 54.49, 51.68, 48.56, 45.90, 27.99, 27.36, 22.89, 20.57, 14.79, 12.14, 8.41, 8.16, 7.18, 6.32, 5.78, 5.07, 4.29, 3.82, 3.43, 2.91, 2.05, 1.75, 1.58, 0.94, 0.53, −0.28, −1.25, −4.82, −18.97, −23.46.

Synthesis of N-ethyl-N,N',N'-tris(3-methylpyridin-2-ylmethyl)ethylene-1,2-diamine iron(II)chloride.PF$_6$ ([L3 Fe(II)Cl]PF$_6$). This synthesis was performed analogously to the synthesis for [L2 Fe(II)Cl]PF$_6$. Starting from N-ethyl-N,N',N'-tris(3-methylpyridin-2-ylmethyl)ethylene-1,2-diamine (L3, 104 mg, 257 μmol) gave the complex [L3 Fe(II)Cl]PF$_6$ (146 mg, 229 μmol, 89%) as a yellow solid.

$^1$H NMR (CD$_3$CN, paramagnetic): δ 165.61, 147.20 119.23, 112.67 92.92 63.14, 57.44, 53.20, 50.43, 47.80, 28.59, 27.09, 22.48, 8.55, 7.40, 3.63, 2.95, 2.75, 2.56, 2.26, 1.75, 1.58, 0.92, 0.74, −0.28, −1.68, −2.68, −12.36, −28.75.

Synthesis of N-benzyl-N,N',N'-tris(3-methylpyridin-2-ylmethyl)ethylene-1,2-diamine iron(II)chloride.PF$_6$ ([L4 Fe(II)Cl]PF$_6$). This synthesis was performed analogously to the synthesis for [L2 Fe(II)Cl]PF$_6$. Starting from N-benzyl-N,N',N'-tris(3-methylpyridin-2-ylmethyl)ethylene-1,2-diamine (L4, 119.5 mg, 257 μmol) gave the complex (172 mg, 229 μmol, 95%) as a yellow solid.

$^1$H NMR (CD$_3$CN, paramagnetic): δ 166.33, 145.09, 119.80, 109.45, 92.94, 57.59, 52.83, 47.31, 28.40, 27.89, 16.28, 11.05, 8.70, 8.45, 7.69, 6.99, 6.01, 4.12, 2.89, 2.71, 1.93, 1.56, −0.28, −1.68, −2.58, −11.40, −25.32.

Experimental

Experiments were carried out in a temperature-controlled glass beaker equipped with a magnetic stirrer, thermocouple and a pH electrode. The bleach experiments are carried out at 40 and 60° C. In examples when formulations are used, the dosage amounted to about 5 g/l total formulation. The composition of the base formulation without bleach is described below:

Detergent Formulation

Anionic surfactant: 9%

Nonionic surfactant: 7%

Soap: 1%

Zeolite: 30%

Polymers: 3%

Sodium carbonate: 7%

Enzyme granules: 1%

Sodium silicate: 5%

Sodium citrate: 3.5%

Dequest® 2047: 1%

Percarbonate: 19%

TAED granule (83%) 5.5%

Water and minors: 8%

In total 8.6 mmol/l $H_2O_2$ was used, dosed in the form of sodium percarbonate. The pH was adjusted at 10.0. The bleaching process took place for 30 minutes.

Tea-stained test cloths (BC-1) were used as bleach monitor. After the bleach experiment, the cloths were rinsed in tap water and dried in a tumble drier. The reflectance ($R_{460}*$) was measured before and after the wash on a Minolta® CM 3700d spectrophotometer. The average was taken of 2 test cloths. The differences in reflectance, expressed as $\Delta R$ values, are given in the tables below.

Example 1

Ligand/metal salt mixtures were dosed at a concentration of 10 μmol/l iron perchlorate and 50 μmol/l of ligand. These mixtures were prepared by dissolving the iron salt and ligand in ethanol. 10 ml of this stock solution was added to the bleach solution.

|  | $\Delta R$: |
|---|---|
| $H_2O_2$ (no buffer): | 7.4 points |
| Fe-perchlorate + L1: | 13.7 points |
| Fe-perchlorate + L2: | 16.8 points |
| Fe-perchlorate + L3: | 16.3 points |
| Fe-perchlorate + L4: | 14.3 points |
| Fe-perchlorate + L5: | 14.0 points |
| Fe-perchlorate + L6: | 13.2 points |
| Fe-perchlorate + L7: | 13.5 points |

These results show a clear benefit of these complexes with respect to the blank. The mixtures using ring-substituted ligands L2 to L5, in particular L2 ("Me-Trilen") and L3 ("Et-Trilen"), show benefit compared with the ring-unsubstituted ligand L1 ("Trispicen").

Example 2

Well-defined metal-ligand complexes were dosed using the same set up as Example 1, except using 10 μM catalyst, at 40° C., with 8.8 mmol/l $H_2O_2$, no buffer, pH 10.0:

|  | $\Delta R$: |
|---|---|
| no catalyst: | 6.5 points |
| [Fe(L2)Cl]PF$_6$: | 15.7 points |
| [Fe(L3)Cl]PF$_6$: | 14.8 points |
| [Fe(L4)Cl]PF$_6$: | 12.7 points |

Example 3

Well-defined metal-ligand complexes were dosed using the same set up as Example 2, at 40° C., except using 5 μM catalyst, with 8.8 mmol/l $H_2O_2$ in 10 mmol/l carbonate buffer, pH 10.0:

|  | $\Delta R$: |
|---|---|
| no catalyst: | 7.4 points |
| [Fe(L2)Cl]PF$_6$: | 15.9 points |
| [Fe(L3)Cl]PF$_6$: | 14.4 points |
| [Fe(L4)Cl]PF$_6$: | 11.3 points |

Example 4

Well-defined metal-ligand complexes were dosed using the same set up as Example 3, at 40° C., except in the presence of 5 g/L detergent formulation without TAED (8.8 mmol/l $H_2O_2$, pH 10.0):

|  | $\Delta R$: |
|---|---|
| no catalyst: | 8.6 points |
| [Fe(L2)Cl]PF$_6$: | 14.9 points |
| [Fe(L3)Cl]PF$_6$: | 14.4 pointts |
| [Fe(L4)Cl]PF$_6$: | 11.1 points |

Example 5

Well-defined metal-ligand complexes were dosed using the same set up as Example 3, except in the presence of 5 g/L detergent formulation with TAED (yielding 8.7 mmol/l $H_2O_2$ and 2 mmol/l peracetic acid):

|  | $\Delta R$: |
|---|---|
| no catalyst: | 11.3 points |
| [Fe(L2)Cl]PF$_6$: | 19.6 points |
| [Fe(L3)Cl]PF$_6$: | 17.4 points |

Example 6

Well-defined metal-ligand complexes were dosed using the same set up as Example 3, but at 60° C.:

|  | $\Delta R$: |
|---|---|
| no catalyst: | 12.7 points |
| [Fe(L2)Cl]PF$_6$: | 21.6 points |
| [Fe(L3)Cl]PF$_6$: | 19.1 points |
| [Fe(L4)Cl]PF$_6$: | 15.3 points |

Example 7

Well-defined metal-ligand complexes were dosed using the same set up as Example 6, at 60° C., except in the presence of 5 g/L detergent formulation without TAED:

|  | ΔR: |
|---|---|
| no catalyst: | 14.2 points |
| [Fe(L2)Cl]PF$_6$: | 20.5 points |
| [Fe(L3)Cl]PF$_6$: | 18.8 points |
| [Fe(L4)Cl]PF$_6$: | 16.5 points |

These results show that the well-defined Fe-ligand complexes provide high bleaching activity, similar to those of Fe-salt/ligand mixtures. The activity ranks as Me-Trilen>Et-Trilen>Bz-Trilen. The complex catalysts are also active in detergent formulations, with or without TAED. Also, the complex catalysts are active at 60° C., both in the absence or presence of a formulation.

The structures of the ligands L1 to L7 is shown below:

L1
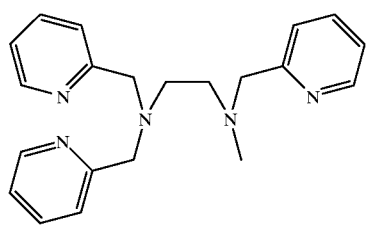

L2
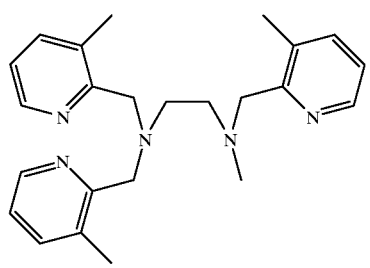

L3
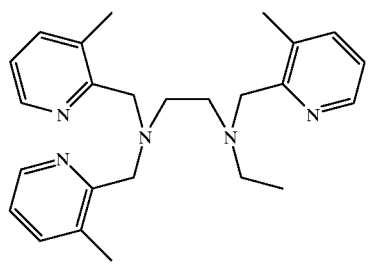

L4
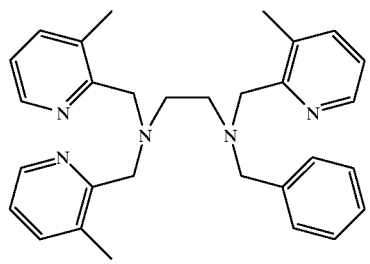

L5
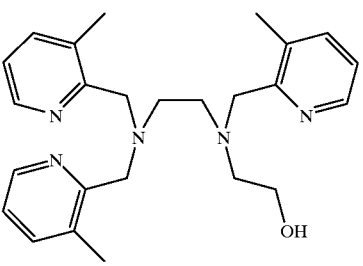

L6
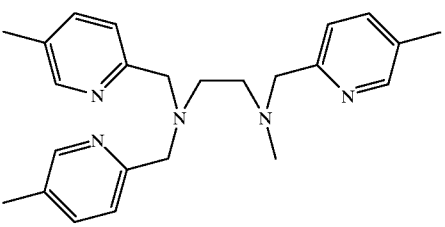

L7
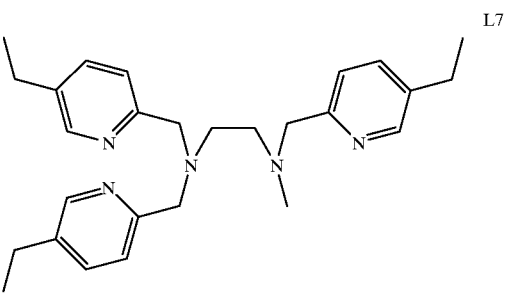

What is claimed is:

1. A bleach and oxidation catalyst comprising a complex of the general formula (A):

$$[LMX_n]^z Y_q \qquad (A)$$

in which

M represents iron in the II, III, IV or V oxidation state, manganese in the II, III, IV, VI or VII oxidation state, or copper in the I, II or III oxidation state;

X represents a coordinating species;

n represents zero or an integer in the range from 0 to 3;

z represents the charge of the complex and is an integer which can be positive, zero or negative;

Y represents a counter ion, the type of which is dependent on the charge of the complex;

q=z/[charge Y];

L represents a pentadentate ligand of general formula (B):

$$R^1R^1N-W-NR^1R^2 \qquad (B)$$

wherein each $R^1$ independently represents $-R^3-V$, in which $R^3$ represents an optionally substituted group selected from the group consisting of alkylene, alkenylene, oxyalkylene, aminoalkylene and alkylene ether, and V represents a substituted heteroaryl group selected from the group consisting of pyridinyl, pyrazinyl, pyrazolyl, imidazolyl, benzimidazolyl, pyrimidinyl, triazolyl and thiazolyl;

W represents an optionally substituted alkylene bridging group selected from the group consisting of $-CH_2CH_2-$, $-CH_2CH_2CH_2-$, $-CH_2CH_2CH_2CH_2-$ and $-CH_2-C_6H_4-CH_2-$;

$R^2$ represents an alkyl or aryl group optionally substituted with a substituent selected from the group consisting of hydroxy, alkoxy, carboxylate, carboxamide, carboxylic ester, sulphonate, amine, alkylamine and $N^+(R^4)_3$, wherein $R^4$ is selected from the group consisting of hydrogen, alkanyl, alkenyl, arylalkanyl, arylalkenyl, oxyalkanyl, oxyalkenyl, aminoalkanyl, aminoalkenyl, alkanyl ether and alkenyl ether.

2. A catalyst according to claim 1, wherein M is iron in the II, III, IV or V oxidation state.

3. A catalyst according to claim 1, wherein W represents ethylene.

4. A catalyst according to claim 1, wherein V represents substituted pyridin-2-yl.

5. A catalyst according to claim 1, wherein $R^3$ represents methylene and V represents methyl-substituted or ethyl-substituted pyridin-2-yl.

6. A catalyst according to claim 4, wherein V represents 3-methyl pyridin-2-yl.

7. A catalyst according to claim 1, wherein $R^2$ represents a group selected from the group consisting of methyl, ethyl, benzyl, 2-hydroxyethyl and 2-methoxyethyl.

8. A catalyst according to claim 7, wherein $R^2$ represents methyl or ethyl.

9. A catalyst according to claim 1, wherein the ligand L is N-methyl-N,N',N'-tris(3-methyl-pyridin-2-ylmethyl) ethylene-1,2-diamine or N-ethyl-N,N',N'-tris(3-methyl-pyridin-2-ylmethyl)ethylene-1,2-diamine.

10. A catalyst according to claim 1, wherein X represents a coordinating species selected from the group consisting of $CH_3CN$, $H_2O$, $F^-$, $Cl^-$, $Br^-$, $OOH^-$, $O_2^{2-}$, $O_2^-$, $R^5COO^-$, $R^5O^-$, $LMO^-$, and $LMOO^-$ wherein $R^5$ represents hydrogen or optionally substituted phenyl, naphthyl, or $C_1$–$C_4$ alkyl.

11. A catalyst according to claim 1, wherein the counter ion Y is selected from the group consisting of $R^6COO^-$, $ClO_4^-$, $BF_4^-$, $PF_6^-$, $R^6SO_3^-$, $R^6SO_4^-$, $SO_4^{2-}$, $NO_3^-$, $F^-$, $Cl^-$, $Br^-$, and $I^-$, wherein $R^6$ represents hydrogen or optionally substituted phenyl, naphthyl or $C_1$–$C_4$ alkyl.

12. A composition comprising a ligand L or a ligand L-generating species, and a salt of the metal M, wherein a catalyst as defined in claim 1 is formed in situ.

13. A composition comprising a peroxy bleaching compound and a catalyst as defined in claim 1.

14. A composition according to claim 13, which comprises the peroxy bleaching compound at a level of from 2 to 35% by weight and the catalyst at a level corresponding to a metal content of from 0.0005 to 0.5% by weight.

15. A composition according to claim 13, wherein the peroxy bleaching compound is selected from the group consisting of hydrogen peroxide, hydrogen peroxide-liberating or—generating compounds, peroxyacids and their salts, and mixtures thereof, optionally together with peroxy-acid bleach precursors.

16. A composition according to any of claims 13, further comprising a surface-active material and a detergency builder.

17. A composition according to claim 16, comprising the surface-active material in an amount of from 10 to 50% by weight, and the detergency builder in an amount of from 5 to 80% by weight.

* * * * *